United States Patent [19]

Duffett

[11] Patent Number: Plant 5,819

[45] Date of Patent: Dec. 2, 1986

[54] CHRYSANTHEMUM PLANT NAMED YELLOW FAVOR

[75] Inventor: William E. Duffett, Salinas, Calif.

[73] Assignee: Yoder Brothers, Inc., Barberton, Ohio

[21] Appl. No.: 675,567

[22] Filed: Nov. 28, 1984

[51] Int. Cl.[4] ..... A01H 5/00

[52] U.S. Cl. ..... Plt./78

[58] Field of Search ..... Plt./78

*Primary Examiner*—R. E. Bagwill

*Attorney, Agent, or Firm*—Schwartz, Jeffery, Schwaab, Mack, Blumenthal & Evans

[57] ABSTRACT

A Chrysanthemum plant named Yellow Favor having flat capitulum form; decorative capitulum type; yellow ray floret color; diameter across face of capitulum ranging from 8 to 12 cm. at maturity; uniform nine week photoperiodic flowering response to short days; medium plant height when grown as a pinched pot mum, and spreading branching pattern that adapts to both disbud and spray pot programs.

3 Drawing Figures

The present invention comprises a new and distinct cultivar of *Chrysanthemum morifolium,* Ramat., named Yellow Favor.

Yellow Favor is a product of a planned sport induction program which had the objective of creating a new Chrysanthemum cultivar that would expand the color range of an existing cultivar while retaining all other original traits.

Yellow Favor was discovered and selected by William E. Duffett in March 1982 in a controlled environment in Salinas, Calif. as one flowering plant, a color variant within a flowering block established as rooted cuttings from stock plants which had been exposed as unrooted cuttings to an X-ray source of 1000 rads. The irradiated cultivar was Favor, disclosed in U.S. Plant Pat. No. 5,227 and originated by the present inventor.

The first act of asexual reproduction of Yellow Favor was accomplished when vegetative cuttings were taken from the initial selection in June 1982 in a controlled environment in Salinas, Calif. by a technician working under formulations established and supervised by William E. Duffett. Horticultural examination of selected units initiated September 1982 has demonstrated that the combination of characteristics as herein disclosed for Yellow Favor are firmly fixed and are retained through successive generations of asexual reproduction.

Yellow Favor has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Yellow Favor which in combination distinguish this Chrysanthemum as a new and distinct cultivar:

(1) Flat capitulum form.

(2) Decorative capitulum type.

(3) Yellow ray floret color.

(4) Diameter across face of capitulum ranging from 8 to 12 cm. at maturity.

(5) Uniform nine week photoperiodic flowering response to short days.

(6) Medium plant height, requiring 2 long day weeks prior to pinch and short days, and 1 to 2 applications of 2500 ppm B-9 SP, the first at 14, the second at 21 days after the beginning of short days to attain a flowered plant height of 25 to 35 cm. in 6" pots.

(7) Spreading branching pattern that adapts to both disbud and spray pot programs.

The accompanying photographic drawings depict typical foliage and inflorescence characteristics of Yellow Favor.

Sheet 1 is a color photograph of two plants of Yellow Favor. The plant shown in the upper left was grown as a pinched spray, and the lower a pinched disbud, with colors being as accurate as possible with renditions of this type.

Sheet 2 is a black and white photograph of three views of the inflorescence of Yellow Favor.

Sheet 3 shows the upper and under surface of the leaves of Yellow Favor in three stages of development (mature, intermediate and immature).

Of the many commercial cultivars known to the present inventor the most similar in comparison to Yellow Favor is Yellow Torch, disclosed by U.S. Plant Pat. No. 3,421. Reference is made to attached Chart A which compares certain characteristics of Yellow Favor to those same characteristics of Yellow Torch.

The color of Yellow Favor is clear, devoid of bronze tinging. The branching pattern is significantly more spreading. The plant height is taller. The diameter of the capitulum is greater. The capitulum form, type and flowering response period are similar.

In the following description, color references are made to The Royal Horticultural Society Colour Chart. The color values were determined between 9:15 and 9:30 a.m. on June 19, 1984 under 380 foot-candle light intensity at Salinas, Calif.

Classification:

*Botanical.*—*Chrysanthemum morifolium,* Ramat., cv Yellow Favor.

*Commercial.*—Decorative disbud and spray pot mum.

I. INFLORESCENCE

A. Capitulum:

*Form.*—Flat.

*Type.*—Decorative.

*Diameter across face.*—8 to 12 cm.

B. Corolla of ray florets:

*Color* (*General tonality from a distance of three meters*).—Yellow.

*Color* (*upper surface*).—3A oxidizing to 6B.

*Color* (*under surface*).—8A, 8B.

*Shape.*—Broad with rounded tip, scattering of tubular rays.

C. Corolla of disc florets:

*Color* (*mature*).—154B.

*Color* (*immature*).—145B.

D. Reproductive organs:

*Androecium.*—Present disc florets only; scant pollen.

*Gynoecium.*—Present both ray and disc florets.

II. PLANT

A. General Appearance:

*Height.*—Medium, requiring 2 long day weeks prior to pinch and short days, and 1–2 applications of 2500 ppm B-9 SP, the first at 14, the second at 21 days after the beginning of short days to attain a flowered plant height of 25 to 35 cm. in 6″ pots.

*Branching pattern.*—Spreading.

B. Foliage:

*Color* (*upper surface*).—147A.

*Color* (*under surface*).—147B.

*Shape.*—Shallow lobed, moderately serrated.

CHART A

COMPARISON OF YELLOW FAVOR AND YELLOW TORCH

| CULTIVAR | RAY FLORET COLOR | CAPITULUM FORM AND TYPE | BRANCHING PATTERN |
|---|---|---|---|
| YELLOW FAVOR | YELLOW | FLAT DECORATIVE | SPREADING |
| YELLOW TORCH | YELLOW TINGED BRONZE | FLAT DECORATIVE | UPRIGHT |

| CULTIVAR | DIAMETER ACROSS FACE OF CAPITULUM | PLANT HEIGHT | FLOWERING RESPONSE PERIOD |
|---|---|---|---|
| YELLOW FAVOR | 8 to 12 cm. | MEDIUM 25 to 35 cm. | 9 WEEKS |
| YELLOW TORCH | 7.5 to 10 cm. | SHORT 20 to 30 cm. | 9 WEEKS |

COMPARISONS MADE OF PLANTS GROWN AS PINCHED DISBUD POT MUMS IN SALINAS, CALIFORNIA AND LEAMINGTON, ONTARIO, CANADA

I claim:

1. A new and distinct cultivar of *Chrysanthemum morifolium,* Ramat., plant named Yellow Favor, as described and illustrated, and particularly characterized as to uniqueness by the combined characteristics of flat capitulum form; decorative capitulum type; yellow ray floret color; diameter across face of capitulum ranging from 8 to 12 cm. at maturity; uniform nine week flowering response; medium plant height, and spreading branching pattern that adapts to both disbud and spray pot mum programs.

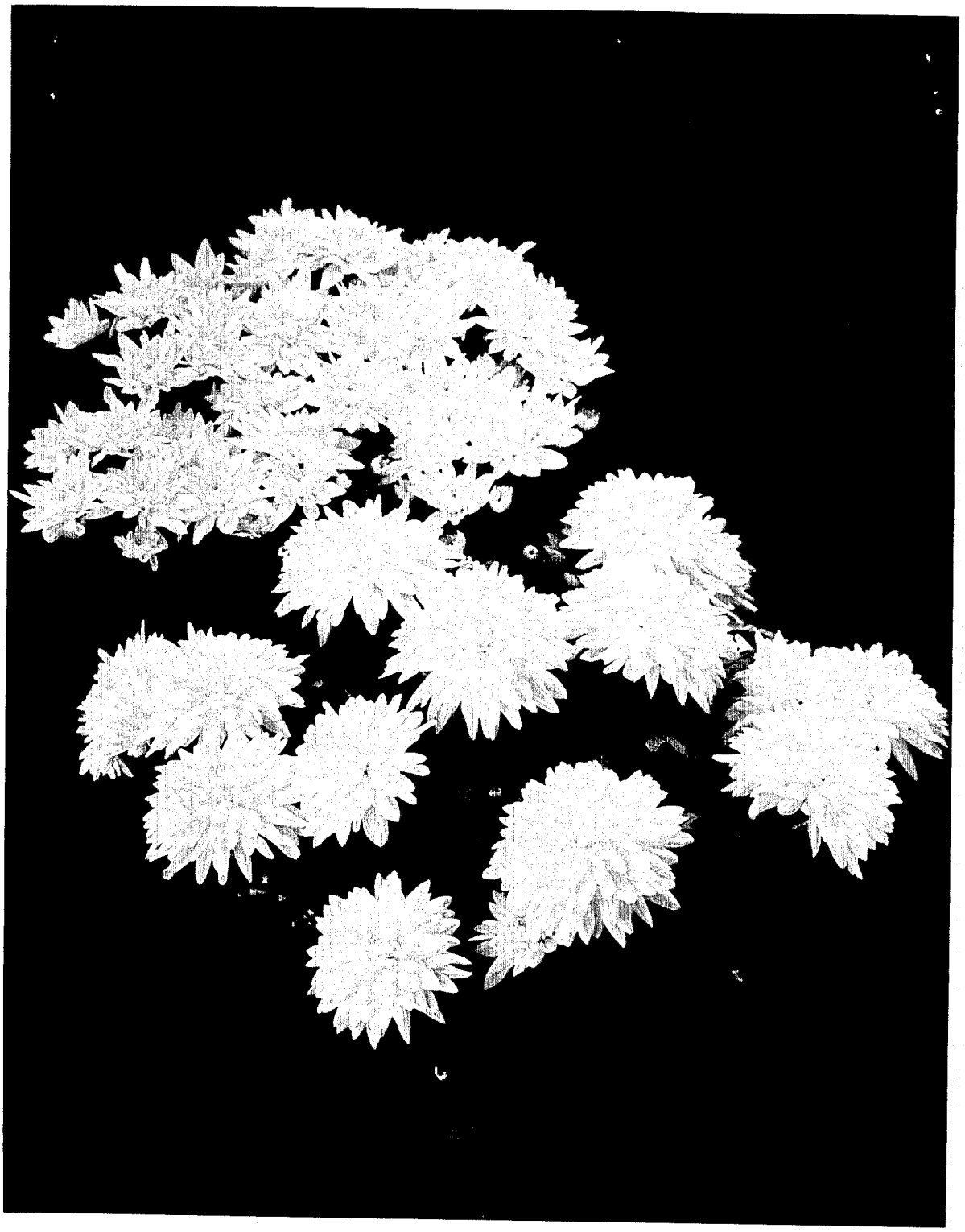

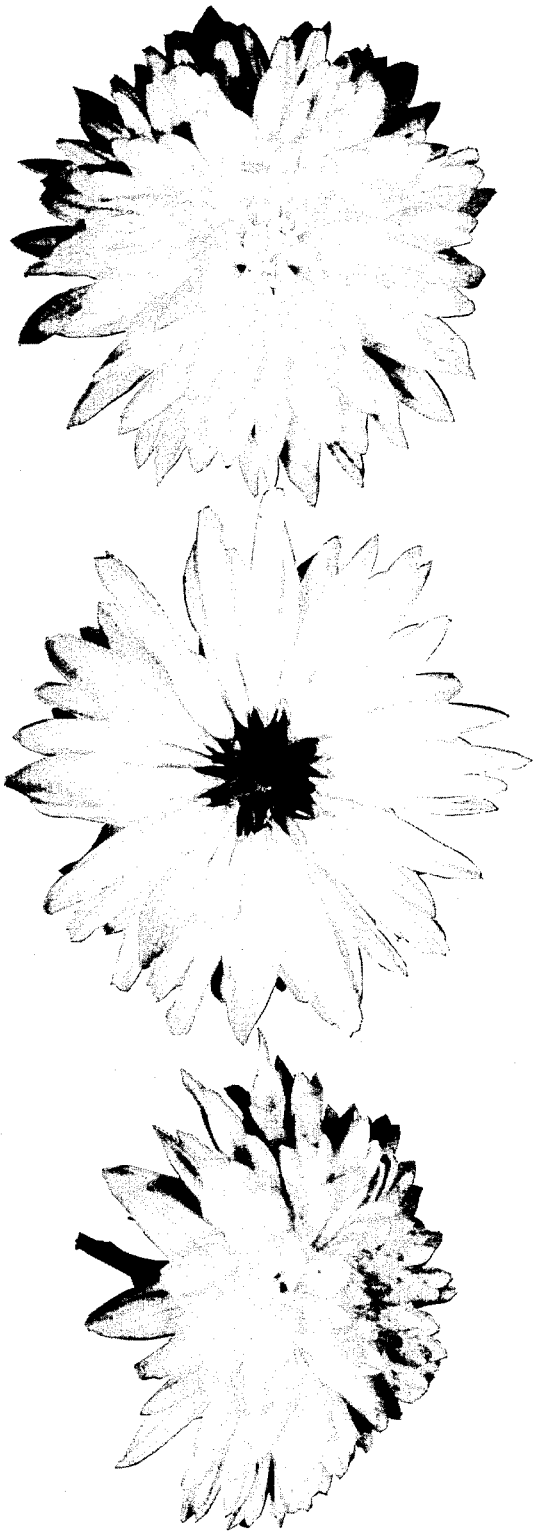

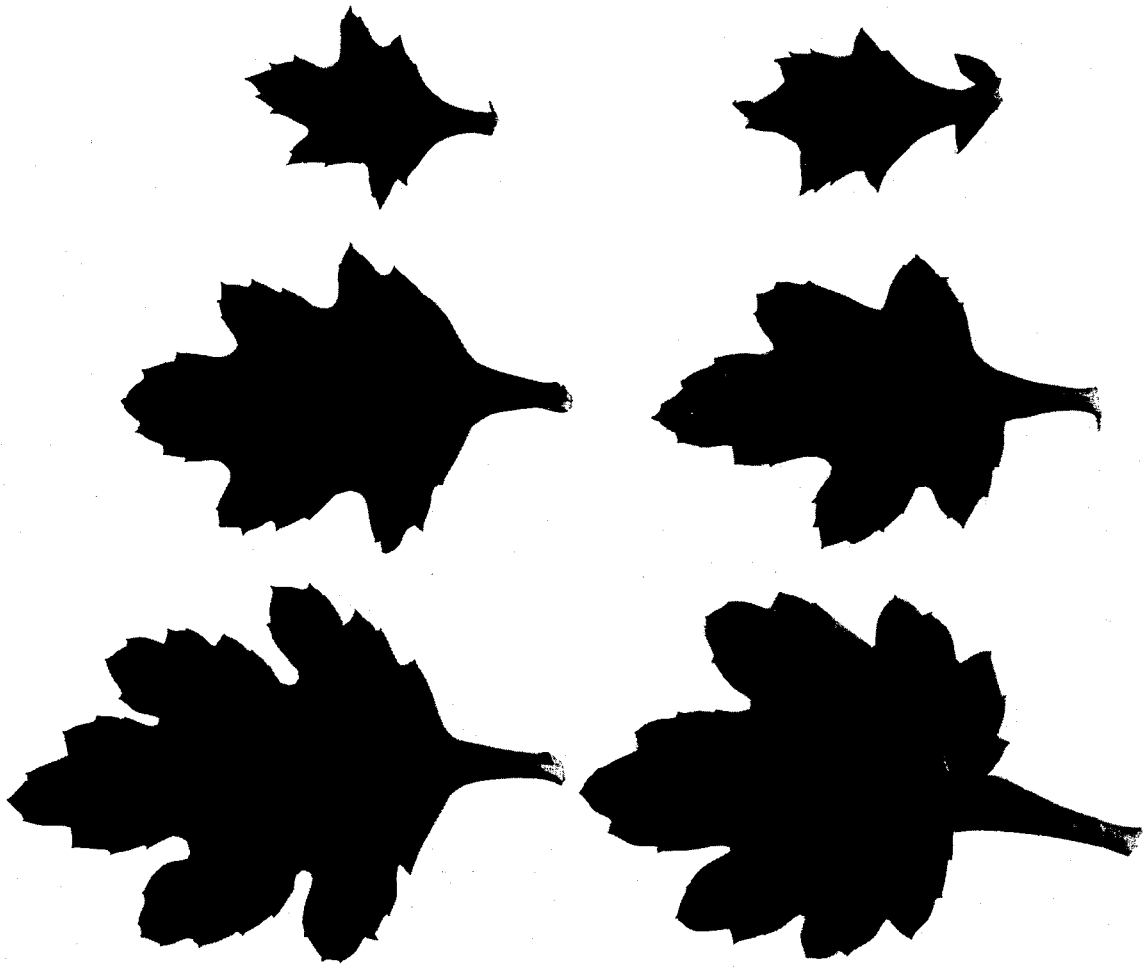

* * * * *